United States Patent [19]

Zhou et al.

[11] Patent Number: 5,276,110
[45] Date of Patent: Jan. 4, 1994

[54] HIGHLY REGULAR MULTI-ARM STAR POLYMERS

[75] Inventors: Lin-Lin Zhou, Lansdale, Pa.; Paul M. Toporowski, Ottawa; Jacques Roovers, Gloucester, both of Canada

[73] Assignee: National Research Council of Canada, Ottawa, Canada

[21] Appl. No.: 928,368

[22] Filed: Aug. 12, 1992

[51] Int. Cl.$^5$ .............................................. C08F 283/00
[52] U.S. Cl. ................................... 525/479; 525/474; 528/15; 528/25; 528/26; 528/27; 528/31; 528/35
[58] Field of Search .................... 525/63, 479, 474; 526/279; 528/15, 31, 25, 26, 35

[56] References Cited

U.S. PATENT DOCUMENTS

| | | | |
|---|---|---|---|
| 4,507,466 | 3/1985 | Tomalia et al. | 528/332 |
| 4,857,630 | 8/1989 | Kim | 528/397 |
| 5,132,375 | 7/1992 | Satori et al. | 525/474 |

FOREIGN PATENT DOCUMENTS 258065  3/1988  European Pat. Off. .
460556 12/1991  European Pat. Off. .

OTHER PUBLICATIONS

Macromolecules 1980 vol. 13 pp. 191-193 N. Hadjichristidis et al, Star Branched Polymers, 4. Synthesis of 18-Arm Polyisoprenes.
Macromolecules 1989 vol. 22 pp. 1897-1903 J. Roovers et al, Synthesis and Characterization of Multiarm Star Polybutadienes.
Angew. Chem. Int. Ed. Engl. 1990 vol. 29 pp. 138-175 D. A. Tomalia et al, Starburst Dendrimers.
Macromolecules 1992 vol. 25 pp. 5561-5572 Y. H. Kim et al, Hyperbranched Polyphenylenes.

*Primary Examiner*—Ralph H. Dean
*Attorney, Agent, or Firm*—Alan A. Thomson

[57] ABSTRACT

A carbosilane-based hybrid star polymer having a carbosilane core of large size and addition polymer chains emanating from the core, is described. The carbosilane core is formed from a central silane nucleus and built up by repeated alternating hydrosilylation of reactive vinylic sites followed by vinylation of silicon halide reactive sites. The core is reacted with living addition prepolymers to form the hybrid star polymer. The minimum core size to give the desired properties corresponds to that having at least about 48 reactive silicon halide sites on the periphery. These highly regular hybrid star polymers have unique solution and gelling agent properties and form highly structured and rigid gels, and also act as viscosity modifiers. The large carbosilane core having either vinyl or silicon halide reactive sites can be used as a reactive intermediate.

17 Claims, No Drawings

HIGHLY REGULAR MULTI-ARM STAR POLYMERS

FIELD OF THE INVENTION

This invention relates to a class of branched polymers containing a hybrid of a dendritic carbosilane core and star-branched arms of addition polymers. Unique gelling properties have been observed when the core is of a selected large size. The preparation of the novel core is carried out by extended alternating hydrosilylation and vinylic group insertion starting with a carbosilane nucleus. When the reactive core is of sufficient size, it is reacted with living prepolymers to attach individual arms extending from the core surface in star-form.

BACKGROUND AND PRIOR ART

Several types of star-shaped polymers have been prepared recently. The more conventional star polymers have a random molecular structure characterized by lack of symmetry, cross-linking between arms and a large molecular volume. The viscosity of the bulk polymer itself generally is higher than that of any solution thereof. More recently certain highly symmetrical, dense, non-cross-linked star polymers have been described (see for instance U.S. Pat. No. 4,507,466 Mar. 26, 1985 Tomalia et al). In this patent, a regular dendritic star structure was formed by condensation polymerization of an electrophilic monomer with a nucleophilic monomer e.g. dendritic polyamidoamine formed from ammonia, methylacrylate and excess ethylene diamine, with further alternating reaction with the latter two reactants. These dendritic stars are not amenable to the addition of living prepolymerized chains to the end of each arm because the whole dendrite is reactive toward reagents used to create the living end and irregular grafting over the entire structure would occur. A review of this latter type of star polymer is given in Angew. Chem. Int. Ed. Engl. 29 (1990) p. 138–175 Tomalia et al.

Initial work has been done on certain hybrid star polymers in which the starting dendritic structure is an octa-, dodeca-, or decaoctachlorosilane and linear arms are attached at the chloro sites using living prepolymers of isoprene (see Macromolecules 13(1980) p. 191–193 Hadjichristidis et al). Substantially complete reaction at the chloro sites was achieved. See also Macromolecules 22(1989) p. 1897–1903 Roovers et al.

We have continued to investigate this type of hybrid star polymer and have found that an anomaly in solution properties occurs when the chlorosilane core is built up in layers until at least about 48 peripheral active sites for arm linkage is achieved.

SUMMARY OF THE INVENTION

Highly regular multi-arm hybrid star polymers have been formed from carbosilane cores having multiple layers of silane groups and arms of addition polymer chains attached only at the core periphery with the number of arms being at least about 48. With this large core and large number of addition polymer arms, unexpected solution properties have been found.

The invention covers a carbosilane-based hybrid star polymer comprising:
carbosilane core having a central silane nucleus and multiple carbosilane branches extending outwardly from the central nucleus and each peripheral branch having a peripheral silane terminus; and
b) arms of addition polymer chains emanating out from core peripheral silane termini, the number of addition polymer arms being at least about 48.

The core comprises a regular structure of polyalkyl- or polyalkylarylsilane segments. Each peripheral silane terminus in the core rim has two or three outwardly extending dendritic arms of addition polymer chains. The silicone atoms in the core are located in distinct layers and the number of layers or generations may range from 3 to 5 or more, as long as at least 48 addition polymer linkage sites are located in the outer periphery.

The central silane nucleus may be a monosilane or a polysilane initially having either reactive Si-halide sites or reactive vinylic sites.

The invention includes the hybrid star polymer in solvent therefor in the form of a gel.

The invention further includes a process of preparing a carbosilane-based hybrid star polymer comprising:
i) hydrosilylating a silane nucleus having at least two vinyl or substituted vinyl groups with a chloro—or bromo—monohydrosilane to form a 1st generation core reactant having Si—Cl or -Br reactive sites,
ii) vinylating the 1st generation core reactant with a vinyl-or substituted vinyl-Grignard or-lithium reagent to form a 1st generation core reactant having vinyl reactive sites,
iii) repeating the hydrosilyation to form a 2nd generation core reactant having Si—Cl or —Br reactive sites,
iv) continuing the alternating vinylation and hydrosilylation for a sufficient number of generations to yield a carbosilane core having at least 48 peripheral Si—Cl or —Br reactive sites, and
v) reacting the peripheral Si—Cl or —Br reactive sites with living addition prepolymer to attach at least 48 arms of addition polymer chains and form the hybrid star polymer.

The invention also comprises a carbosilane star polymer intermediate having a central silane nucleus and carbosilane branches extending outwardly from the central nucleus, and having at least 48 peripheral Si—Cl or —Br reactive sites.

DETAILED DESCRIPTION

The carbosilane core has a regular dendritic structure free of cross-linking. The dendrimer core is built up in stages or generations from a central silane nucleus by alternating hydrosilylation and vinylation reactions.

The starting nucleus may be an unsaturated monosilane such as alkyltrivinyl- or tetravinylsilane, and tetraallylsilane. Alternatively, an unsaturated disilane such as an alkylene-bis-alkyltrivinylsilane can serve as nucleus. The unsaturated group can be any vinylic group subject to hydrosilylation including vinyl, allyl and styryl groups. The alkylene moiety can be any having 1–6 carbon atoms. Saturated alkyl groups (1–4 C atoms) or aryl groups (phenyl or substituted phenyl) complete the silicon valences. The substituents on the phenyl may be alkyl, alkoxy, phenyl or halide groups.

The hydrosilylation reagent is a halosilane having at least one, preferably at least two, halogen groups attached to silicon. The halogen group may be chloride or bromide. This silane usually is a monosilane such as H$Si(R)_{3-m}Cl_m$ where m=1, 2 or 3, preferably m=2 or 3.

However, a disilane such as H Si(R)$_2$(—CH$_2$—CH$_2$—)$_p$—Si(R)$_{3-m}$Cl$_m$
where
R=alkyl (1–4 C) or aryl (phenyl or substituted phenyl)
m=1, 2 or 3, preferably 2 or 3,
p=0, 1, 2, 3 or 4 may be used. The substituents on the phenyl ring may be alkyl, alkoxy, phenyl or halide groups.

The vinylation reagent may be a Grignard such as CH$_2$=CH Mg Br, CH$_2$=CH—CH$_2$ MgBr and CH$_2$=CH 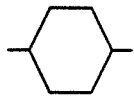

Mg Br, or a lithium reagent such as CH$_2$=CH—Li, CH$_2$=CH—CH$_2$Li and CH$_2$=CH 

Li.

The core synthesis proceeds by hydrosilylation of the nucleus to introduce active silicon halide sites, and each of these sites is reacted to attach a vinylic group. These vinylic groups then are hydrosilylated to introduce second generation silicon halide sites, and this is continued until at least 48 active silicon halide sites are present on the periphery of the core. The reactions are controlled to go to substantial completion at each stage so that successive layers of silane branching sites are formed at the periphery. This gives a dense, dendritic, non-cross-linked core structure with all reactive sites towards the periphery. Because of the reactions involved, only the desired active sites are reacted and the interior dendritic arms remain unreacted and uncross-linked. The number of generations to achieve at least 48 peripheral silicon halide sites usually is from 3 to 5, depending on the nucleus and reagents chosen.

It has been found important that the core synthesis proceed until at least about 48 reactive silicon halide sites are formed at the periphery. When addition polymer arms are attached to each of these sites an anomaly in solution properties of the resulting star polymer has been found to occur. With lower numbers of addition polymer arms e.g. 18 and 32, the solution properties are such that soft gels are formed, the gels being softer and more fluid than the parent (undissolved) polymer. When the number of addition polymer arms is at least about 48 (preferably 64–128), an unusually enhanced gelling power is observed such that very rigid, solid gels are formed in solution, these gels being more rigid and much less fluid than the parent (undissolved) star polymer. This can be illustrated by measuring the modulus and viscosity as in Example 5 below, and the intensity of scattering maxima as in Example 6 below.

The outer arms of addition polymer are attached to each of the active silicon halide sites in the periphery of the core. This is accomplished by anionic addition polymerization to preform a living polymer suitably of molecular weight at least about 1000 preferably from about 5000 to about 100,000. These prepolymers have a living end and can be coupled to the reactive silicon halide site in the core. The coupling is controlled to go to completion and to occur only at these halide sites so that a very regular dendritic or star-form structure is achieved.

To form the addition prepolymer for the outer arm, monomers that are susceptible to termination—free anionic polymerization may be used. The living polymer end should be capable of electrophilic substitution at the chlorosilane (or bromosilane) site. Suitable anionic polymerization techniques, reagents and operative monomers are given in: Encyclopedia of Polymer Science and Engineering, Second Edition 1985 Vol. 2 Page 1 (Chapter on Anionic Polymerization by S. Bywater) J.I. Kroschwitz Ed.-in-Chief, Publisher: Wiley Interscience. Examples of suitable monomers are styrene, α-methylstyrene, paratertiary-butylstyrene, para-dimethyl-t-butylsiloxystyrene, N,N bis (trimethylsilyl) p-aminostyrene, 2-vinylpyridine, 4-vinylpyridine and alkyl-substituted vinylpyridines, butadiene, isoprene, 2,3-dimethylbutadiene, cyclic ethers (e.g. ethylene oxide, propylene oxide), and cyclic sulfides (e.g. ethylene sulfide, propylene sulfide).

These monomers may be used to form living homopolymers or copolymers including random or block copolymers. It is possible to preform the block copolymer and couple it to the core as in Example 2, or to couple different polymers in sequence as in Example 3. The living polymers may be formed to have various substituent groups which will not interfere with the coupling reaction at the Si—Cl site. These groups may be at the end of the chain remote from the living end (e.g. by starting each chain with a substituted initiator) or within the chain (by copolymerization e.g. with an amine-, siloxy- or ester-substituted monomer). Examples of initiators having suitable substituent groups are dimethylaminopropyllithium and 5-ethoxy-4-oxo-hexyllithium.

These substituent groups on the living polymer may be selected for the purposes of introducing polar groups to affect solubility or introducing reactive sites for further reaction.

It is possible to render the hybrid star polymer or part thereof water-soluble by incorporating groups such as alcohol, carboxylic acid, or amine groups into the addition polymer arms. This can be accomplished by use of substituted monomers e.g. hydrolysis of incorporated p-dimethyl-t-butylsiloxystyrene, the latter used as monomer or comonomer in forming the addition polymer. Similarly amine groups can be present in the monomer or comonomer; or protected carboxylic acid groups stable under the polymerization conditions can be present and later hydrolyzed to acid.

The living addition polymer normally is a straight chain type. However, it is possible to form branches in the living addition polymer by suitable modifiers, e.g. the addition of various amines and ethers affect the microstructure of anionically polymerized dienes. In particular the addition of dipiperidinoethane produces almost exclusively living 1,2-polybutadiene.

A 48-arm hybrid star polymer may be formed by starting with tetravinylsilane as nucleus, hydrosilylating with dichloromethylsilane, vinylating with vinyl-MgBr, again hydrosilylating with dichloromethylsilane, followed by vinylating, and finally hydrosilylating with trichlorosilane which gives a core with 48 active Si—Cl sites. Living prepolymer then is coupled at these sites to form 48 addition polymer arms. By choosing the hydrosilylation reagent at each stage it is possible to vary considerably the number of core peripheral sites and the number of generations needed. We have found that numbers of addition polymer arms from about 64–128 are most suitable.

The hybrid star polymers, where the addition polymer arms are hydrocarbon, are soluble in solvents in which the linear polymer is soluble, such as aliphatic and aromatic hydrocarbon solvents, chlorinated hydrocarbon solvents, ether solvents and ketone solvents. These polymers, usually in amounts from about 1 to 30% wt/vol, form solid gels with these solvents, the gels being more rigid than the polymers alone. Selected polymers may also act as gelling agents in polar organic solvents such as dimethylformamide and dimethylsulfoxide. The polymers can be used as gelling agents in organic solvent-based paints and coating compositions. The polymers can be used as sorption agents for good solvents therefor e.g. in solvent spill clean-up the solvent can be solidified for easy removal. Depending on the nature of the addition polymer arms, the hybrid star polymers are compatible with various rubbers and plastic molding compositions. Where the addition polymer arms comprise polystyrene, the hybrid star polymers are useful as impact resistance improvers for polystyrene molding compositions. Where the addition polymer arms comprise butadiene polymer, the star polymers are useful as mixing promoters or microinterface controllers in blends comprising butadiene polymer rubbers. The star polymers also are useful as viscosity modifiers in extrusion and injection molding composition. In some cases the star polymers will serve as crystallinity modifiers in crystalline polymeric materials. The star polymers can be used in lubricating oils as viscosity modifiers or shear resistance improvers. The star polymers are also suitable calibrating agents of membrane and filter pore sizes since the diameter of the star polymers can be accurately determined.

When the hybrid star polymer is water-soluble e.g. by having groups such as pyridine, hydroxystyrene, p-aminosytrene incorporated in the addition polymer arms, these star polymers can be used as gelling agents or thickeners in latex paints and various aqueous coating compositions. Gels formed using these star polymers have thixotropic properties in both aqueous and organic solvent systems. In some cases the star polymers can serve as emulsifiers and in others as de-emulsifiers. In some slurry systems, the star polymers will serve as flocculants.

The carbosilane core having at least 48 peripheral active silicon halide sites can serve as a reactive intermediate for instance in a kit with appropriate solvents for the purpose of modifying the molecular weight and molecular weight distribution of a batch of living polymer. This reactive core intermediate should be stored under anhydrous conditions e.g. in sealed ampoules.

The molecular weight of the hybrid star polymer usually is at least about 50,000 daltons. Depending on the number and size of the addition polymer arms and the size of the core, the molecular weight may range up to about 10,000,000 daltons. At room temperature the hybrid star polymers are viscous liquids or solids depending on the number of arms, the molecular weight of the arms and the chemical composition of the arms.

In the following examples, all parts and percentages are by weight unless otherwise indicated.

EXAMPLE 1 a) Preparation Of First Generation Core Reactant I

Into a 100 mL flask was added 2.7 g (20 mmol) of tetravinylsilane (Nucleus), 10.1 g (88 mmol) of dichloromethylsilane (branch site), 40 mL of anhydrous THF (tetrahydrofuran) and 4 drops (about 75 µL) of platinum divinyltetramethyldisiloxane complex in xylene as catalyst. The reaction system was heated to about 50° C. by a heating mantle. The heating mantle was removed (sometimes a cooling bath was needed) as soon as the reaction solution started to reflux (exothermic reaction). The temperature was controlled at about 50° C. to let the exothermic reaction go smoothly. After the exothermic period, the heating mantle was replaced to keep the temperature at 50° C. for 4 hr. After cooling to room temperature, the reaction flask was connected to a vacuum system. The excess dichloromethylsilane and all THF were removed. The product I was taken up in 40 mL of fresh anhydrous THF which was transferred into the flask through the vacuum system.

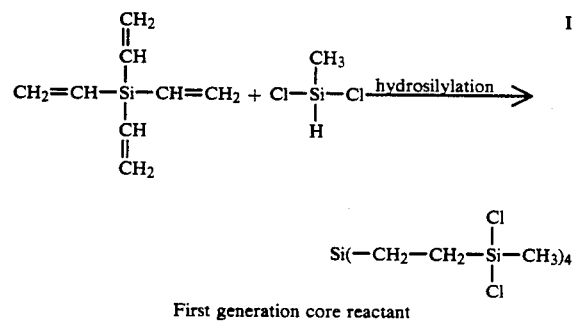

First generation core reactant

This core reactant I has 8 reactive sites (Si-Cl's) for later arm attachment.

b) Preparation OF 2nd Generation Core Reactant III

A solution of core reactant I in THF [as prepared under Example 1a)] was added (dropwise) into a freshly made vinyl magnesium bromide (Grignard reagent 192 mmol) in 120 mL THF. The mixture was stirred at room temperature overnight. Then about 200 mL hexane was added, the mixture was washed with 200 mL water three times and with saturated NaCl solution twice. The organic solution was dried over anhydrous $MgSO_4$. After the solvent was removed through evaporation, the 11 g residue was purified by flash chromatography on a silica gel column eluted with a solution of 0.8% of ethyl acetate in hexane to give 5.5 g of pure oily intermediate (II) overall in a 55% yield.

Into a 100 mL flask was added 2.6 g (5 mmol) of intermediate II, 5.1 g (55 mmol) of dichloromethylsilane, 40 mL of anhydrous THF and 4 drops (about 75 µL) of platinum divinyltetramethyldisiloxane complex in xylene as catalyst. The reaction system was heated to about 50° C. by a heating mantle. The heating mantle was removed (sometimes a cooling bath was needed) as soon as the reaction solution started to reflux (exothermic reaction). The temperature was controlled to let the exothermic reaction go smoothly. After the exothermic period, the heating mantle was replaced to keep the temperature at 50° C. for 4 hr. After cooling to room temperature, the reaction flask was connected to a vacuum system. The excess dichloromethylsilane and all THF were removed, and 40 mL of fresh anhydrous THF was transferred to the flask through the vacuum system. The two reactions are illustrated as follows.

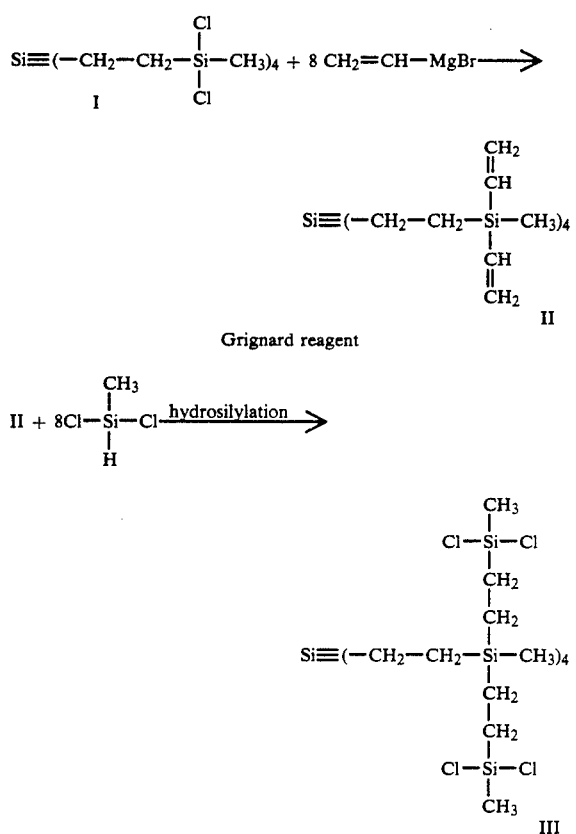

Grignard reagent

This second generation core reactant III has 16 reactive sites (Si—Cl's) for later arm attachment.

c) Preparation of 3rd Generation Core Reactant V

The solution of III prepared under Example 1(b) was dropwise added into a freshly made vinyl magnesium bromide (96 mmol) in 60 mL THF. The mixture was stirred at room temperature overnight. Then about 200 mL hexane was added, the mixture was washed with 200 mL water three times and with saturated NaCl solution twice. The organic solution was dried over anhydrous MgSO$_4$. After the solvent was removed through evaporation, the 6.8 g residue was purified by flash chromatography on a silica gel column eluted with a solution of 0.8% of ethyl acetate in hexane to give 3.1 g of pure oily intermediate IV in 48% overall yield.

Into a 100 mL flask was added 1.9 g (1.4 mmol) of intermediate IV, 3.2 g (28 mmol) of dichloromethylsilane, 30 mL of anhydrous THF and 3 drops (about 50 μL) of platinum divinyltetramethyldisiloxane complex in xylene. The reaction system was heated to about 50° C. by a heating mantle. The heating mantle was removed as soon as the reaction solution started to reflux (exothermic reaction). The temperature was controlled to let the exothermic reaction go smoothly. After the exothermic period, the heating mantle was replaced to keep the temperature at 50° C. for 4 hr. After cooling to room temperature, the reaction flask was connected to a vacuum system. The excess dichloromethylsilane and all THF were removed, and 30 mL of fresh anhydrous THF was transferred to the flask through the vacuum system yielding a solution of 3rd generation core reactant V.

This 3rd generation core reactant V has 32 reactive sites (Si—Cl's) for later arm attachment.

d) Preparation Of 4th Generation Core Reactant VII and 64-Arm Hybrid Dendrimer Polybutadiene VIII This 3rd generation core reactant V was reacted with the vinyl Grignard reagent as described above to form intermediate VI, and VI reacted with dichloromethylsilane as described above to form 4th generation core reactant VII having 64 reactive Si—Cl sites.

Under anhydrous and oxygen-free conditions 17.6 g of 1,3-butadiene were added to 150 mL benzene and polymerized anionically at room temperature with 0.160 g sec-BuLi ($2.5 \times 10^{-3}$ mole) to form living polymer. After 24 hours 85 mg ($1.280 \times 10^{-5}$ mole) of Fourth Generation core reactant VII (64 reactive sites) was added. The coupling reaction of polymer arm to core reactant VII was essentially complete after 6 days at room temperature as indicated by size exclusion chromatography. Excess unreacted arm material was removed by fractional precipitation in benzenemethanol.

Calculated arm polybutadiene molecular weight = 7,000 daltons; Observed $M_n$ = 6300 by osmometry.

Molecular weight of hybrid star polymer VIII by light scattering $M_w$ = 395 000 daltons.

Number of arms in hybrid star VIII f = 63. Yield was 33%.

EXAMPLE 2

Preparation Of 64-Arm Hybrid Star Poly(styrene-b-butadiene) IX

To 200 mL benzene were added 9.5 g of styrene and 60 mg of sec-BuLi. Polymerization was allowed to proceed for 48 hrs. at room temperature. Then 18.7 g of butadiene was added and polymerization continued for 24 hrs. at room temperature. To this polymer solution was added 34 mg of the 4th generation chlorosilane dendrimer (core reactant VII). The resulting hybrid star block copolymer IX was characterized by size exclusion chromatography and the size corresponding to the 64 arm hybrid was confirmed. Weight fraction of styrene in IX was 34.7% by UV analysis. Yield of IX was 35.5%. This block copolymer would be a useful additive to improve the impact resistance of polystyrene moldings.

EXAMPLE 3

Preparation Of Mixed 64-Arm Hybrid Star Poly(1,4-butadiene-m-1,2-butadiene) X

To 150 mL benzene were added 17 g 1,3-butadiene and 16 mg sec-BuLi. Polymerization was allowed to proceed for 24 hrs. after which 59 mg of 4th generation core reactant VII was added. After 3 days the resulting solution was subdivided, and 25 mL containing 2.8 g of polymer were added to a living poly(butadienyllithium) solution prepared separately from 5 g of 1,3-butadiene, and 32 mg sec-BuLi in the presence of 386 mg dipiperidinoethane at 4° C. The resulting hybrid mixed star polymer X was recovered after 6 days and purified by fractionation in benzene-methanol. Yield was 1.92 g. NMR $^1$H analysis indicated 79.5 weight % 1,4-polybutadiene content. This hybrid polymer can be used to promote mixing and blend compatibility in various polybutadiene rubber blends.

EXAMPLE 4

Preparation Of 128-Arm Hybrid Star Polybutadiene XIII

The 4th generation core reactant VII was reacted with the vinyl Grignard reagent as described above to form intermediate XI, and XI then reacted with dichloromethylsilane as described above to form 5th generation core reactant XII having 128 reactive Si—Cl sites.

To 50 mL benzene were added 8.4 g of butadiene and 77 mg of sec.-BuLi. Polymerization was allowed to proceed for 24 hrs. at room temperature. To this solution was added 2.76 mL of a benzene solution of 5th generation core reactant XII containing 0.142 mole/L of Si—Cl bonds. The resulting 128-arm star polymer XIII was characterized by size exclusion chromatography after 7 days and the size was indicative of the 128-arm star. Molecular weight by light scattering is 340,000 daltons. Yield of this hybrid star polybutadiene XIII was 37.9%.

EXAMPLE 5

Use as a gelling agent is illustrated.

A 15% by weight solution in methylcyclohexane of the hybrid star polymer VIII prepared in Example 1(d) had a complex shear modulus of $1.2 \times 10^\alpha$ dyn/cm, at a shear rate of 1 rad/s at room temperature. The bulk modulus of this polymer (i.e. undiluted, solvent free) at the same frequency and temperature was $2 \times 10^3$ dyn/cm$^2$.

This same solution had a shear viscosity of $1.9 \times 10^2$ Pa.s measured in the oscillatory mode at 10 rad/s. The shear viscosity was $1.0 \times 10^3$ Pa.s and $4.4 \times 10^3$ Pa.s at 1 rad/s and 0.1 rad/s respectively. The newtonian viscosity of this same polymer in the solvent-free state was $2 \times 10^2$ Pa.s over the same frequency range.

This confirms that the hybrid star polymer is a very effective gelling agent since the gels behave more like solids than the parent (undissolved) polymers. The opposite is true for the hybrid star polymers having 32 or less addition polymer arms.

EXAMPLE 6

Evidence For Structured Gels

Semi-dilute solutions containing from 1 to 35% preferably 10 to 20% of the hybrid star polymer VIII prepared in Example 1(d) dissolved in deuterated methylcyclohexane showed scattering maxima when investigated by small angle neutron scattering. From the Bragg angles of the maxima, repeat lengths of between 100 and 250Å were calculated. The absolute intensity of the scattering maxima was 2.85, which is characteristic of macrocrystalline ordering (For elaboration see J.P. Hansen and L. Verlet, Phys. Rev. 184, 151 [1969])

This evidence indicates that in these solutions the centers of the hybrid star polymer molecules were regularly spaced in 3 dimensions at distances of 100 to 250Å from each other. This distance varied depending on the molecular weight and solution concentration of the polymer. The values of the absolute intensity of the scattering maxima for the smaller hybrid star polymers were significantly less e.g. for the 18-arm stars and 32-arm stars they were 1.5 and 1.6 respectively. This unexpectedly large increase (to 2.85 for the 64-arm star) is indicative of a high degree of macrocrystalline ordering and highly structured gel formation absent in the lower arm star polymer solutions. Thus these hybrid star polymers would be useful in dripless paints and other coating applications where highly structured gels are advantageous.

The embodiments of the invention in which an exclusive property or privilege is claimed are defined as follows:

1. A carbosilane-based hybrid star polymer comprising:
   a) a carbosilane core having a central silane nucleus and multiple carbosilane branches extending outwardly from the central nucleus and each branch having a peripheral silane terminus; and
   b) arms of polymer chains emanating out from core peripheral silane termini, the number of polymer arms being at least about 48, said polymer chains being derived from living polymers formed by anionic polymerization.

2. The hybrid star polymer of claim 1 wherein each peripheral silane terminus in the core has two or three outwardly extending arms of addition polymer chains.

3. The hybrid star polymer of claim 2 wherein the core comprises a structure of polyalkyl-or polyalkylaryl-silane segments where the alkyl group has from 1 to 4 carbon atoms, and the aryl group is phenyl or alkyl-substituted phenyl.

4. The hybrid star polymer of claim 1 wherein the number of arms attached to peripheral silane termini ranges from about 48 to about 128.

5. The hybrid star polymer of claim 1 wherein the carbosilane core structure has from 3 to 5 successive layers of silane sites.

6. The hybrid star polymer of claim 1 wherein the arms of polymer chains b) have substituents selected from the group consisting of tertiary amine, carboxylic acid and hydroxyl.

7. The hybrid star polymer of claim 1 wherein the arms of polymer chains b) are selected from the group consisting of polymers and copolymers of styrene, butadiene, alkylene oxide, and alkylene sulfide.

8. The hybrid star polymer of claim 4 wherein the number of arms b) is 64 or 128.

9. The hybrid star polymer of claim 1 wherein the nucleus is in the form of a carbosilane-substituted alkyl silane selected from substituted tetraalkylsilane and substituted alkylene-bis-trialkylsilane.

10. The hybrid star polymer of claim 1 in a solvent therefor, in the form of a solid gel.

11. A process of preparing a carbosilane-based hybrid star polymer comprising:
   i) hydrosilylating a silane nucleus having at least two vinylic groups subject to hydrosilylation with a chloro-or bromo-monohydrosilane to form a 1st generation core reactant having Si—Cl or —Br reactive sites,
   ii) vinylating the 1st generation core reactant with a selected vinylic-Grignard or-lithium reagent to form a 1st generation core reactant having vinylic hydrosilylation- reactive sites,
   iii) repeating the hydrosilyation to form a 2nd generation core reactant having Si—Cl or —Br reactive sites,
   iv) continuing the alternating vinylation and hydrosilylation for a sufficient number of generations to yield a carbosilane core having at least 48 peripheral Si—Cl or —Br reactive sites, and
   v) reacting the peripheral Si—Cl or —Br reactive sites with living anionic prepolymer to attach at least 48 arms of polymer chains and form the hybrid star polymer.

12. The process of claim 11 wherein the number of generations to form the core in i)–iv) is from 3 to 5.

13. The process of claim 11 wherein, in step i), tetravinylsilane is hydrosilylated with dichloromethylsilane or trichlorosilane.

14. The process of claim 11 wherein, in step ii), the vinylating reagent is selected from the group consisting of vinylMgBr and vinylLi.

15. The process of claim 11 wherein, in step v), the living anionic prepolymer is selected from polystyrene, poly(vinylpyridine), polybutadiene, polyethylene oxide, polyethylenesulfide, and copolymers thereof.

16. A carbosilane star polymer having a central silane nucleus and carbosilane branches extending outwardly from the central nucleus, and having at least 48 peripheral Si—Cl or —Br reactive sites.

17. The star polymer of claim 16 wherein the number of reactive sites per molecule is 64 or 128.

* * * * *